United States Patent [19]

Bath

[11] Patent Number: 4,744,360
[45] Date of Patent: May 17, 1988

[54] APPARATUS FOR ABLATING AND REMOVING CATARACT LENSES

[76] Inventor: Patricia E. Bath, 4554 Circle View Blvd., Los Angeles, Calif. 90024

[21] Appl. No.: 943,098

[22] Filed: Dec. 18, 1986

[51] Int. Cl.$^4$ ............................................. A61B 17/36
[52] U.S. Cl. .................................. 128/303.1; 128/397; 604/20; 604/35; 604/43
[58] Field of Search .................... 128/303.1, 395, 397, 128/398; 604/22, 20, 35, 43

[56] References Cited

U.S. PATENT DOCUMENTS

| | | | |
|---|---|---|---|
| 3,460,538 | 8/1969 | Armstrong | 128/303.1 |
| 3,971,382 | 7/1976 | Kransov . | |
| 3,982,541 | 9/1976 | L'Esperance, Jr. | 128/303.1 |
| 4,024,866 | 5/1977 | Wallach | 604/22 |
| 4,320,761 | 3/1982 | Haddad | 604/22 |
| 4,538,608 | 9/1985 | L'Esperance, Jr. | 128/395 |
| 4,580,559 | 4/1986 | L'Esperance . | |
| 4,583,539 | 4/1986 | Karlin et al. | 128/395 |

OTHER PUBLICATIONS

"Heatless Laser Etching" by John Free; Popular Science 12/83.
Serial No. 702,569 filed 2-19-85 to Gruen et al.

Primary Examiner—Lee S. Cohen
Assistant Examiner—David Shay
Attorney, Agent, or Firm—Cushman, Darby & Cushman

[57] ABSTRACT

A method and apparatus for removing cataracts in which a flexible line preferably 1 mm or less in diameter is inserted through an incision into the anterior chamber until its end is adjacent the cataract. Coherent radiation, preferably at a frequency between 193 and 351 nm, is coupled to the cataract by an optical fiber in the line. An irrigation sleeve provided about the fiber and an aspiration sleeve extending partially around the irrigation sleeve conduct irrigating liquid to and remove ablated material from the anterior chamber and form with the optical fiber the flexible line.

7 Claims, 1 Drawing Sheet

APPARATUS FOR ABLATING AND REMOVING CATARACT LENSES

BACKGROUND AND SUMMARY OF THE INVENTION

The invention relates to a method and apparatus for coupling laser radiation to a cataract lens in the eye to ablate the same.

Every eye is divided into an anterior and posterior chamber separated by a normally transparent lens which focuses light onto the retina at the back of the posterior chamber. When the lens becomes cloudy for any of a variety of reasons sight is impaired and the cloudy lens must be removed. Following removal of the lens, an inter ocular lens (IOL) implant can be placed in the posterior chamber or thick glasses or contact lenses used to focus the light.

A number of techniques are now in use for this common surgical procedure. An incision can be made in the eye and a sharp instrument inserted to cut and then aspirate by vacuum the cloudy cataract tissue. More recently, a small incision-typically 3 mm-can be made in the eye surface and an ultrasonic probe inserted to a position adjacent the lens. The ultrasonic energy then disintegrates the lens material which can likewise be removed by aspiration.

Laser radiation is now used widely in various surgical techniques particularly those involving the eye. For example, the patent to Krasnov, U.S. Pat. No. 3,971,382, describes a technique in which laser radiation is focused onto the anterior capsule of the lens to form a hole through which the cataract substance can be drawn from the lens capsule.

Optical fibers are also commonly used for medical and other applications to transmit coherent radiation from a laser to some location in the body where material is to be coagulated or disintegrated. U.S. patent application No. 702,569, filed Feb. 19, 1985, describes a micro instrument with an optical fiber. The optical fiber can be inserted into the eye for the removal of abnormal tissue such as tumors. Radiation with a wavelength between 200 and 400 nm is said to be appropriate.

The present invention relates to a method and apparatus in which coherent radiation is transmitted by a flexible line containing an optical fiber is inserted through a limbel incision, preferably 1 mm or less, in the eye surface and then through a 1 mm or less anterior capsulatomy into the lens nucleus. The optical fiber is then positioned within the crystalline lens.

Coherent radiation disintegrates the crystalline material into extremely small particles less than 0.1 mm in diameter. These nuclear particles and cortex can then be irrigated and aspirated from the capsular bag, which is left intact, except for the 1 mm anterior capsulatomy, via an aspiration sleeve which is formed about and extending along the optical fiber. At the same time irrigating liquid is supplied via an irrigation sleeve likewise formed about and extending along the optical fiber.

Since the particles produced by this ablation are so small, the device can be made to be extremely small and therefore, the incision likewise can be made much smaller than with other techniques such as ultrasonic. Utilizing an optical fiber further permits the energy to be more efficiently and effectively focused onto the lens to be removed.

Radiation in the range of 193 to 351 nm has proved to be satisfactory. In particular, 308 nm was found to be the most effective experimental wavelength. However, the invention is also effective at other wavelengths, for example, between 193 nm and 3000 nm.

DETAILED DESCRIPTION OF THE PREFERRED EMBODIMENT

Figure 1:
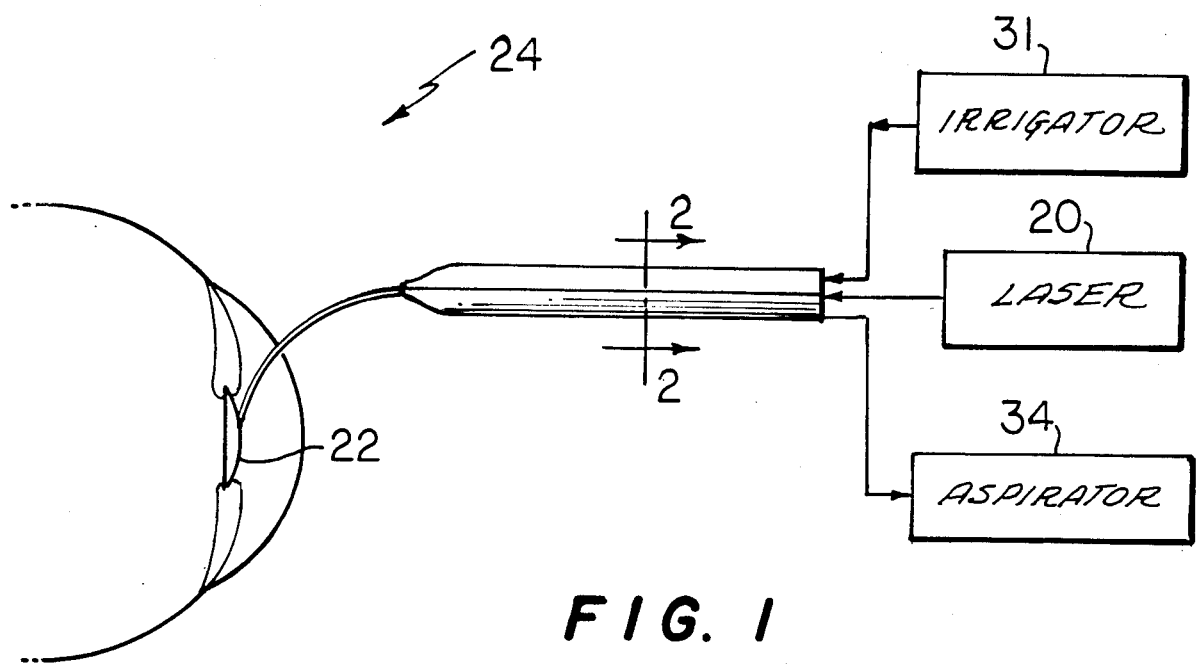
FIG. 1 shows a schematic view of the present invention for ablating a cataract lens.
Figure 2:
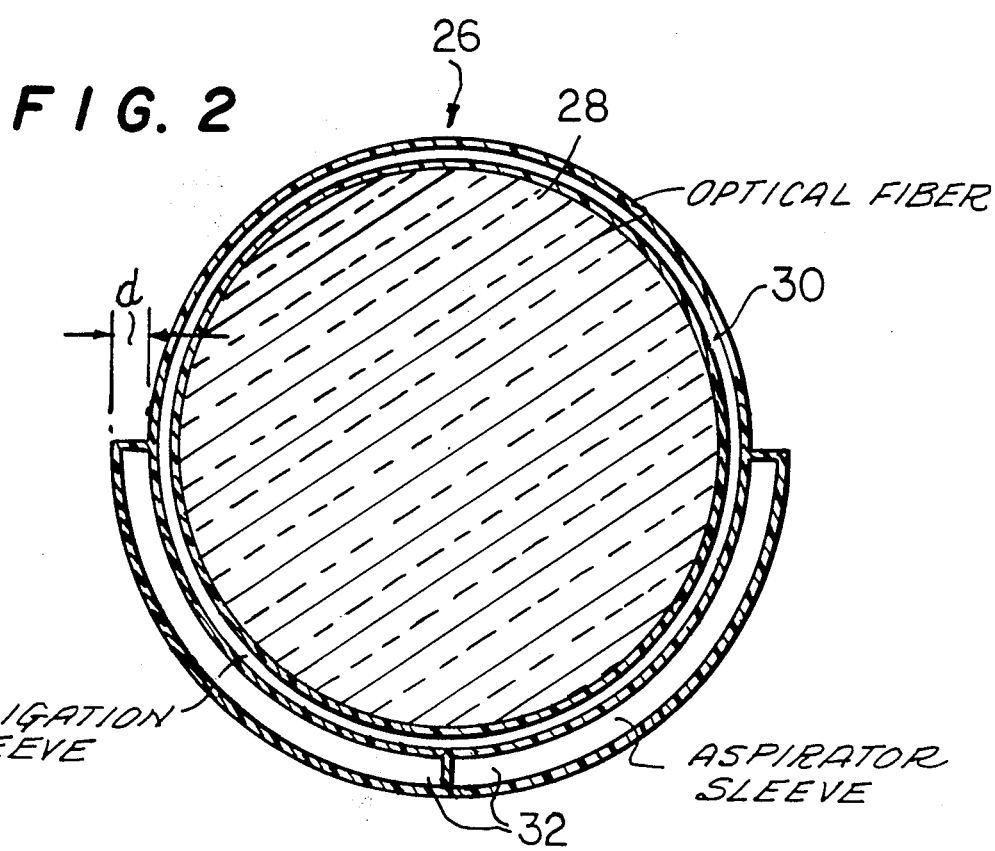
FIG. 2 shows a cross-section of the flexible line of FIG. 1 along the lines 2—2.

Reference is now made to FIGS. 1 and 2 which illustrate a preferred embodiment of the present invention. First, a flexible line 26 is introduced into the interior of the lens nucleus through a 1 mm limbel incision and a 1 mm anterior capsulatomy. Pulsed excimer coherent radiation from a suitable and conventional laser 20 at a suitable energy is coupled to the interior aspect of a cataract lens 22 in a human or animal eye 24 by a flexible line 26 until the desired amount of ablation occurs.

As can be best seen in FIG. 2, flexible line 26 is formed of a conventional optical fiber 28, solid or hollow suitable for medical applications, for example, quartz silica. The ordinary artisan will of course appreciate from a review of this disclosure what materials will be most appropriate for the fiber optics of the probe in view of the particular laser radiation conducted therethrough. The line is then directed successively to the inferior, central and superior areas of the lens nucleus and photoablation again performed at each area. An irrigation sleeve 30 surrounds the optical fiber and is connected to a suitable irrigation device 31 for supplying irrigating liquid to the eye during surgery at a suitable pressure. Aspiration sleeve 32 extends partially around the irrigation sleeve and is likewise coupled to a conventional aspirator 34 for removing by an appropriate suction the minute particles of cataract tissues which are produced in response to incidence of the coherent radiation.

The wavelength of the radiation is preferably in the range as set forth above. Since the particles are so small, the width d of the aspiration sleeve can be 0.3 mm or less. The optical fiber can be made to be no more than 600 microns in diameter and the aspiration sleeve similarly no more than 0.1 mm so that the entire flexible tube 26 can be made of a diameter no greater than 1 mm, permitting the size of the incisions to be minimized.

EXAMPLE

A Lambda Physik 102 Xenon Chloride Excimer laser operating at 308 nm was utilized for these experiments. The laser had unstable resonator optics and rectilinear output aperture producing a 2.2×0.7 beam. The maximum output of the laser was 250 mj. The laser output travelled through a 7 mm hole and was then focused by a quartz lens and optical delivery system which transmitted the optical radiation to the optical fiber (400 mm focal length). The pulse length was 17 nanoseconds and the maximum rep rate was 100 Hertz. By moving the lens, a variation in light flux could be produced. Prior to each irradiation event the pulse energy was measured with a Genetic joulemeter.

Prior to performing ablation the thresholds for ablation of lens nucleus and cortex and bovine lenses was determined.

The target consisted of whole bovine lenses or human lenses with intact lens capsules. Bovine lenses were obtained from freshly enucleated globes using standard microsurgical intracapsular technique. The bovine lenses measured 1 cm in sagittal section, i.e., distance from anterior capsule to posterior capsule. Lenses were tested within 4–8 hours of enucleation.

Human lenses were obtained from freshly enucleated cadaver eyes, preserved by standard moist chamber storage. After excision of the cornea, lenses were delivered using intracapsular microsurgical technique and tested within 12–36 hours post mortem.

Whole lenses were mounted in a 16 mm fixation ring which had a 5 mm aperture. Two methods were utilized to determine the ablation rates. The first method was used for the determination of the ablation rate for the cortex. The entire lens was mounted in the fixation ring and holes were drilled at different energy values, a maximum of 2 mm in the lens. This is essentially equivalent to insertion of an optical fiber during surgery as described above.

For the case of cortex, ablation was essentially absent at energy densities below 7 mj/mm$^2$. In the case of bovine nucleus, the ablation threshold was approximately 10 mj/mm$^2$.

At an energy density of 22 mj/mm$^2$, the ablation rates for bovine cortex and nucleus were 6 microns/pulse and 13 microns/pulse respectively.

At an energy density of 53 mj/mm$^2$, the ablation rates for bovine cortex and nucleus were 42 microns/pulse and 23 microns/pulse, respectively. These differences were statistically significant at the 0.05 level.

The ablation threshold was determined to be approximately 3 mj/mm$^2$. At an energy density of 22 mj/mm$^2$ the ablation rate was approximately 10 microns/pulse. And at energy density of 40 mj/m$^2$ the ablation rate was approximately 40 microns/pulse.

Many changes and modifications of the above described embodiment of the invention can be carried out without departing from the scope of the invention. Accordingly, that scope is intended to be limited only by the scope of the appended claims.

What is claimed is:

1. An apparatus for removing cataracts from an eye comprising:
   a flexible line including an optical fiber for conducting coherent radiation to the cataract and an aspiration sleeve extending at least partially about and along said fiber, the diameter of said line being 1 mm or less;
   a laser means coupled to said fiber for supplying said coherent radiation thereto at a wavelength such that crystalline lens material will be disintegrated into particles less than 0.1 mm in diameter; and
   means for applying suction to said aspiration sleeve for removing ablated cataract material.

2. An apparatus as in claim 1 wherein said laser produces radiation in the wavelength between 193 and 351 nm.

3. An apparatus as in claim 1 further comprising an irrigation sleeve extending wholly around said fiber and wherein said aspiration sleeve extends partially around said irrigation sleeve.

4. An apparatus as in claim 1 wherein the width of said aspiration sleeve is 0.2 mm or less.

5. An apparatus for removing cataracts from an eye comprising:
   a flexible line including an optical fiber for conducting coherent radiation to the cataract, an irrigation sleeve extending at least partially about and along said fiber and an aspiration sleeve extending at least partially about and along said fiber, the width of said aspiration sleeve being 0.3 mm or less and the diameter of said line being 1 mm or less;
   a laser coupled to said fiber for supplying said coherent radiation thereto at a wavelength such that crystalline lens material will be disintegrated into particles less than 0.1 mm in diameter;
   means for supplying an irrigation liquid to said irrigation sleeve; and
   means for applying suction to said aspiration sleeve for removing ablated cataract material.

6. An apparatus as in claim 5 wherein said laser produces radiation in the wavelength between 193 and 351 nm.

7. An apparatus as in claim 5 wherein said irrigation sleeve extends wholly around said fiber and said aspiration sleeve extends partially around said irrigation sleeve.

* * * * *

UNITED STATES PATENT AND TRADEMARK OFFICE
CERTIFICATE OF CORRECTION

PATENT NO. : 4,744,360

DATED : May 17, 1988

INVENTOR(S) : Patricia E. Bath

It is certified that error appears in the above-identified patent and that said Letters Patent is hereby corrected as shown below:

On the title page in the inventor's address, "90024" should be --90043--.

In Column 1, line 16, "inter ocular" should be --intraocular--;

line 25, after "adjacent" --to-- should be inserted;

line 49, "sulatomy" should be --sulotomy--;

line 55, "capsulatomy" should be --capsulotomy--.

In Column 2, line 17, "limbel" should be --limbal--;

line 18, "capsulatomy" should be --capsulotomy--;

line 58, "hole" should be --pinhole--;

line 65, "Genetic" should be --Genetec--.

Signed and Sealed this

Twenty-fifth Day of April, 1989

Attest:

DONALD J. QUIGG

Attesting Officer

Commissioner of Patents and Trademarks